US012718366B2

(12) United States Patent
Vaillant

(10) Patent No.: US 12,718,366 B2
(45) Date of Patent: Aug. 25, 2026

(54) METHODS AND SYSTEMS FOR DYNAMIC INTEGRATION OF COMPUTED TOMOGRAPHY TO INTERVENTIONAL X-RAY IMAGES

(71) Applicant: GE Precision Healthcare LLC, Waukesha, WI (US)

(72) Inventor: Régis Vaillant, Villebon sur Yvette (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 175 days.

(21) Appl. No.: 18/646,514

(22) Filed: Apr. 25, 2024

(65) Prior Publication Data

US 2025/0336163 A1 Oct. 30, 2025

(51) Int. Cl.
*G06T 19/20* (2011.01)
*A61B 34/10* (2016.01)
(Continued)

(52) U.S. Cl.
CPC .............. *G06T 19/20* (2013.01); *A61B 34/10* (2016.02); *G06T 7/11* (2017.01); *G06T 7/13* (2017.01);
(Continued)

(58) Field of Classification Search
CPC ........... G06T 19/20; G06T 7/13; G06T 15/08; G06T 17/00; G06T 2200/04; G06T 2207/10081; G06T 2207/10116; G06T 2207/20081; G06T 2207/20221; G06T 2207/30004; G06T 2210/41; G06T 2219/2004; A61B 34/10; A61B 2034/104; A61B 2034/107
See application file for complete search history.

(56) References Cited

U.S. PATENT DOCUMENTS

| | | | | |
|---|---|---|---|---|
| 9,808,177 B2 * | 11/2017 | Claude | ................. | A61B 5/4566 |
| 2017/0319165 A1 | 11/2017 | Averbuch | | |

FOREIGN PATENT DOCUMENTS

| | | | | |
|---|---|---|---|---|
| CN | 103479376 B | * 10/2015 | ............... | A61B 6/03 |
| JP | 2007325787 A | * 12/2007 | ............... | A61B 6/03 |

OTHER PUBLICATIONS

CN103479376 English Translation; 6 pages.
(Continued)

*Primary Examiner* — Uzma Alam
*Assistant Examiner* — Fani Polyzos Boosalis
(74) *Attorney, Agent, or Firm* — McCoy Russell LLP

(57) ABSTRACT

Various methods and systems are provided for generating a fused image that includes image data captured by a first imaging system and a second imaging system, different from the first imaging system. For example, the method comprises; obtaining three-dimensional (3D) image data of an anatomical region of interest (ROI) of a patient; applying a multi-plane reformation (MPR) tool to the 3D image data to automatically select a slice of the 3D image data that includes the anatomical ROI and corresponds to a view of the anatomical ROI that is shown in a live x-ray image data; fusing the 3D image data with the live x-ray image data without use of a 3D viewer to generate a fused live image comprising 3D image data and live x-ray image data of the anatomical ROI; and outputting the fused live image for display and/or storage.

18 Claims, 13 Drawing Sheets

(51) Int. Cl.
*G06T 7/11* (2017.01)
*G06T 7/13* (2017.01)
*G06T 15/08* (2011.01)
*G06T 17/00* (2006.01)

(52) U.S. Cl.
CPC .............. *G06T 15/08* (2013.01); *G06T 17/00* (2013.01); *A61B 2034/104* (2016.02); *A61B 2034/107* (2016.02); *G06T 2200/04* (2013.01); *G06T 2207/10081* (2013.01); *G06T 2207/10116* (2013.01); *G06T 2207/20081* (2013.01); *G06T 2207/20221* (2013.01); *G06T 2207/30004* (2013.01); *G06T 2210/41* (2013.01); *G06T 2219/2004* (2013.01)

(56) References Cited

OTHER PUBLICATIONS

EP application 25167799.3 filed Apr. 1, 2025—partial Search Report issued Aug. 11, 2025; 17 pages.
JP2007325787 English Translation; 11 pages.
Racadio, J. et al., "Live 3D guidance in the interventional radiology suite," AJR American Journal of Roentgenology, vol. 189, No. 6, Dec. 2007, 8 pages.
Fior, D. et al., "Virtual Guidance of Percutaneous Transthoracic Needle Biopsy with C-Arm Cone-Beam CT: Diagnostic Accuracy, Risk Factors and Effective Radiation Dose," CardioVascular and Interventional Radiology, vol. 42, Jan. 16, 2019, 8 pages.

* cited by examiner

1000

1100

METHODS AND SYSTEMS FOR DYNAMIC INTEGRATION OF COMPUTED TOMOGRAPHY TO INTERVENTIONAL X-RAY IMAGES

FIELD

Embodiments of the subject matter disclosed herein relate generally to interventional image guidance, and more particularly, to methods and systems for dynamic integration of computed tomography (CT) images to interventional X-ray images.

BACKGROUND

A multi-modality imaging system may include one or more different types of medical imaging systems, such as a Positron Emission Tomography (PET) system, a Single Photon Emission Computed Tomography (SPECT) system, a Computed Tomography (CT) system, an ultrasound system, a Magnetic Resonance Imaging (MRI), an X-ray imaging system, or any other system capable of generating tomographic images. One or more of the medical imaging systems may be used to image a subject such as patient, an inanimate object, one or more manufactured parts, and/or foreign objects such as dental implants, stents, and/or contrast agents present within a body. Different types of medical imaging systems may capture different views and/or different characteristics of the subject. A thorough examination of the subject may demand images captured by multiple different medical imaging systems. Deep-learning models and/or other artificial intelligence models can be implemented in the multi-modality imaging system to assist in generating a single tomographic image that includes elements captured by multiple different medical imaging systems.

BRIEF DESCRIPTION

In one embodiment, a method comprises the method comprises; obtaining three-dimensional (3D) image data of an anatomical region of interest (ROI) of a patient; applying a multi-plane reformation (MPR) tool to the 3D image data to automatically select a slice of the 3D image data that includes the anatomical ROI and corresponds to a view of the anatomical ROI that is shown in a live x-ray image data; fusing the 3D image data with the live x-ray image data without use of a 3D viewer to generate a fused live image comprising 3D image data and live x-ray image data of the anatomical ROI; and outputting the fused live image for display and/or storage.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to methods and systems for generating a single tomographic image that include elements captured by multiple different medical imaging systems. First image data of an anatomical region of interest (ROI) of an imaging subject may be acquired using a first imaging modality, and second image data of the ROI of the imaging subject may be acquired using a second imaging modality, different from the first imaging modality. The first image data and the second image data may capture different views, characteristics, and/or elements of the anatomical ROI. For example, the first image data may be computed tomography (CT) image data, and the second image data may be two-dimensional (2D) X-ray image data.

Figure 1:
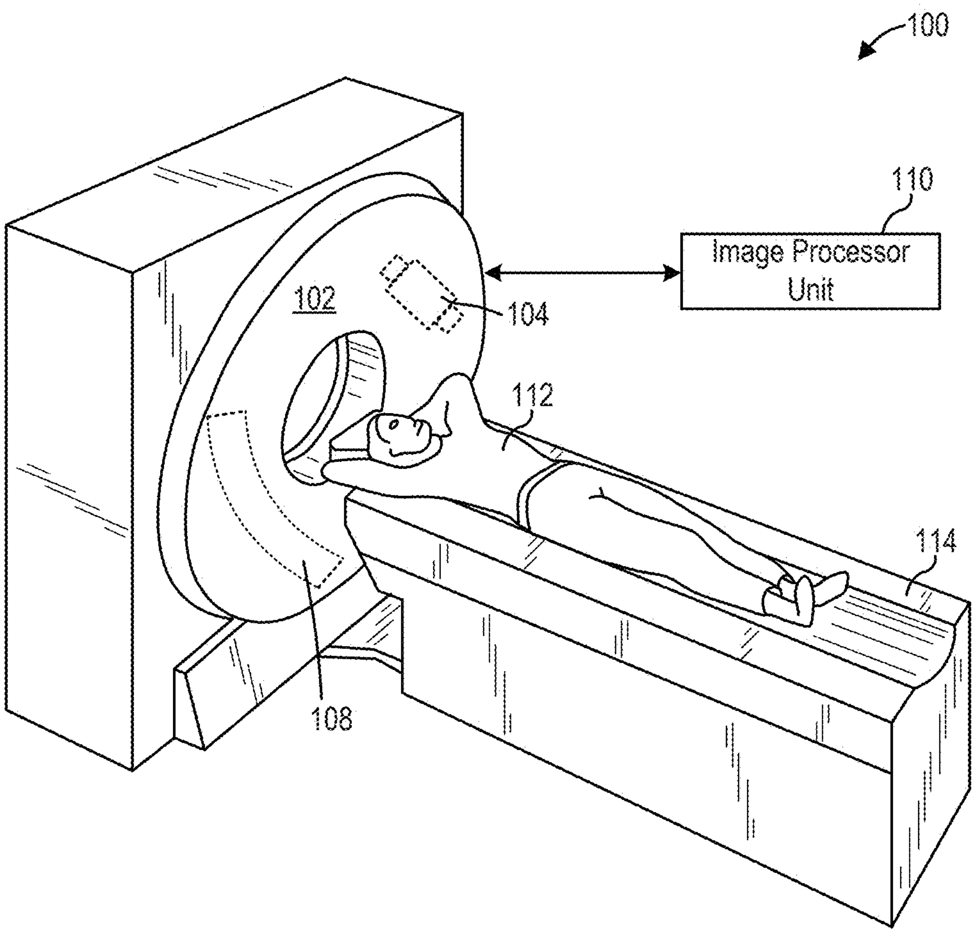
FIG. 1 shows a pictorial view of a computed tomography (CT) imaging system, according to an embodiment.
Figure 2:
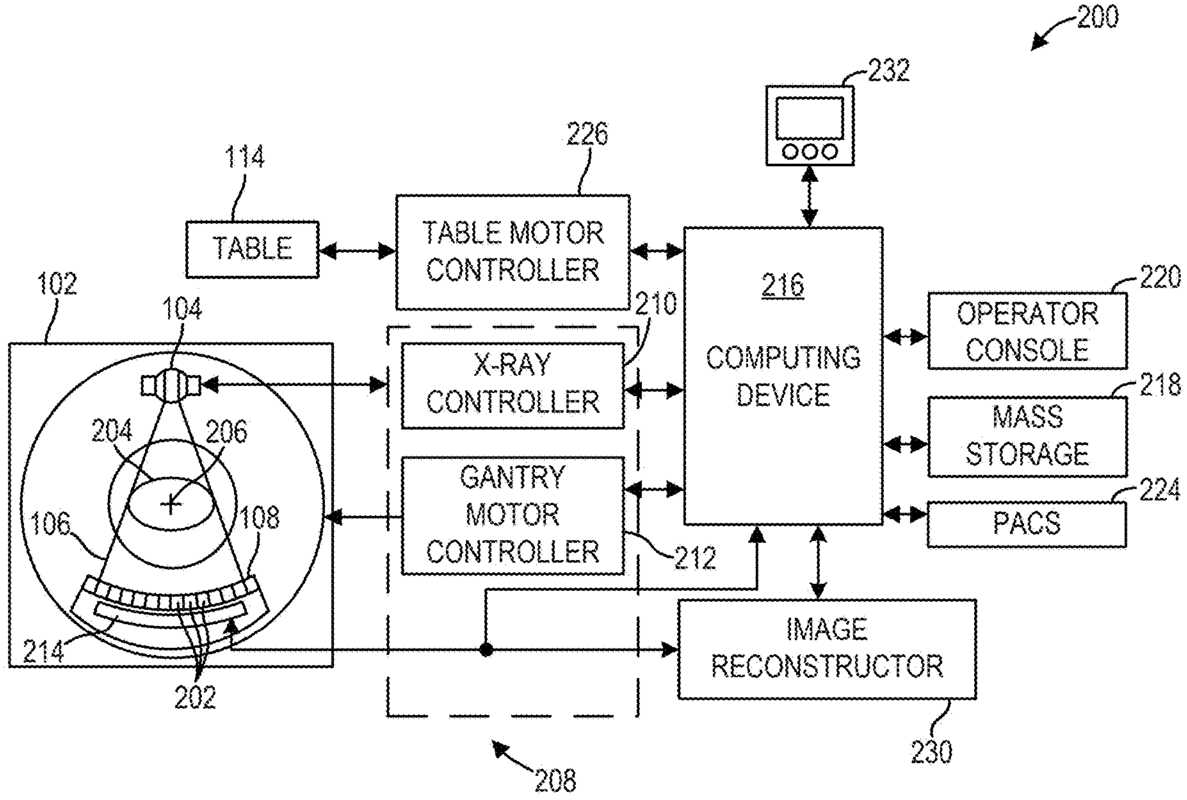
FIG. 2 shows a block schematic diagram of an exemplary X-ray imaging system, according to an embodiment.
Figure 3:
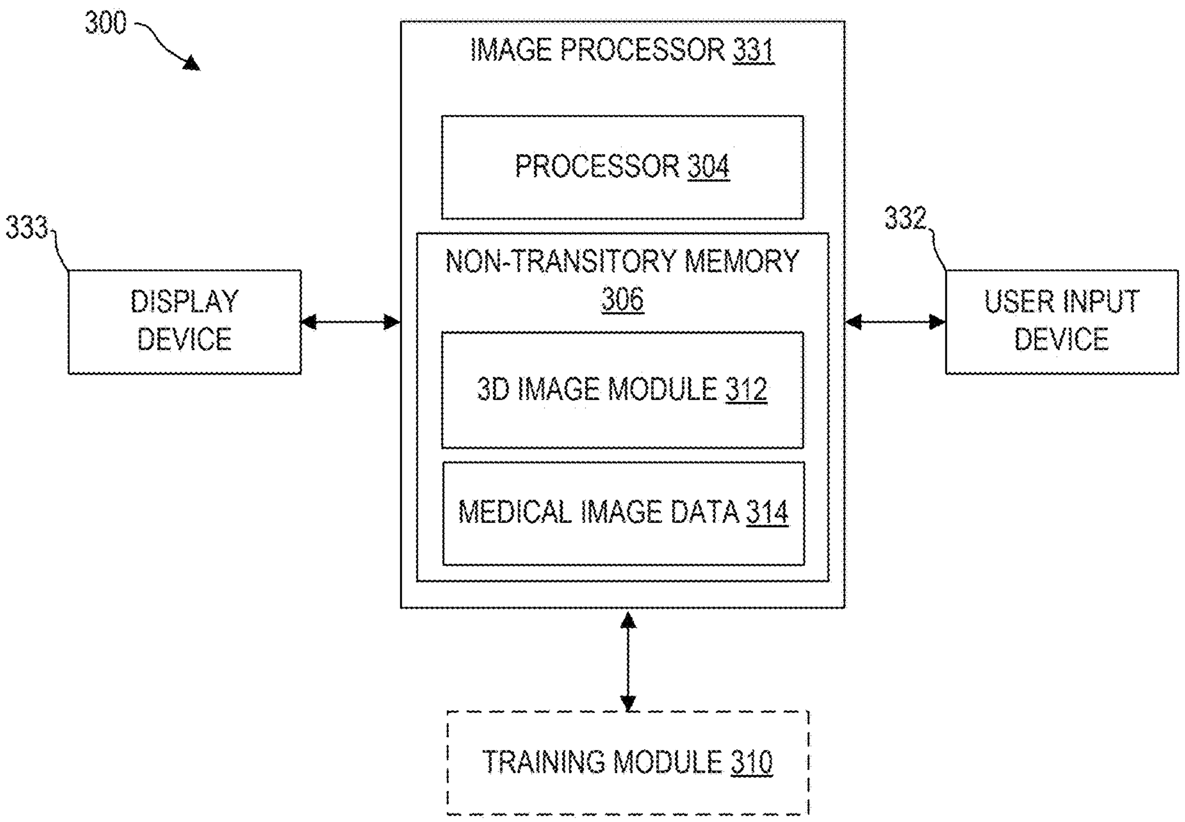
FIG. 3 shows a block diagram of an image processing system configured to generate a single tomographic image that include elements captured by multiple different medical imaging systems, according to an embodiment.
Figure 4:
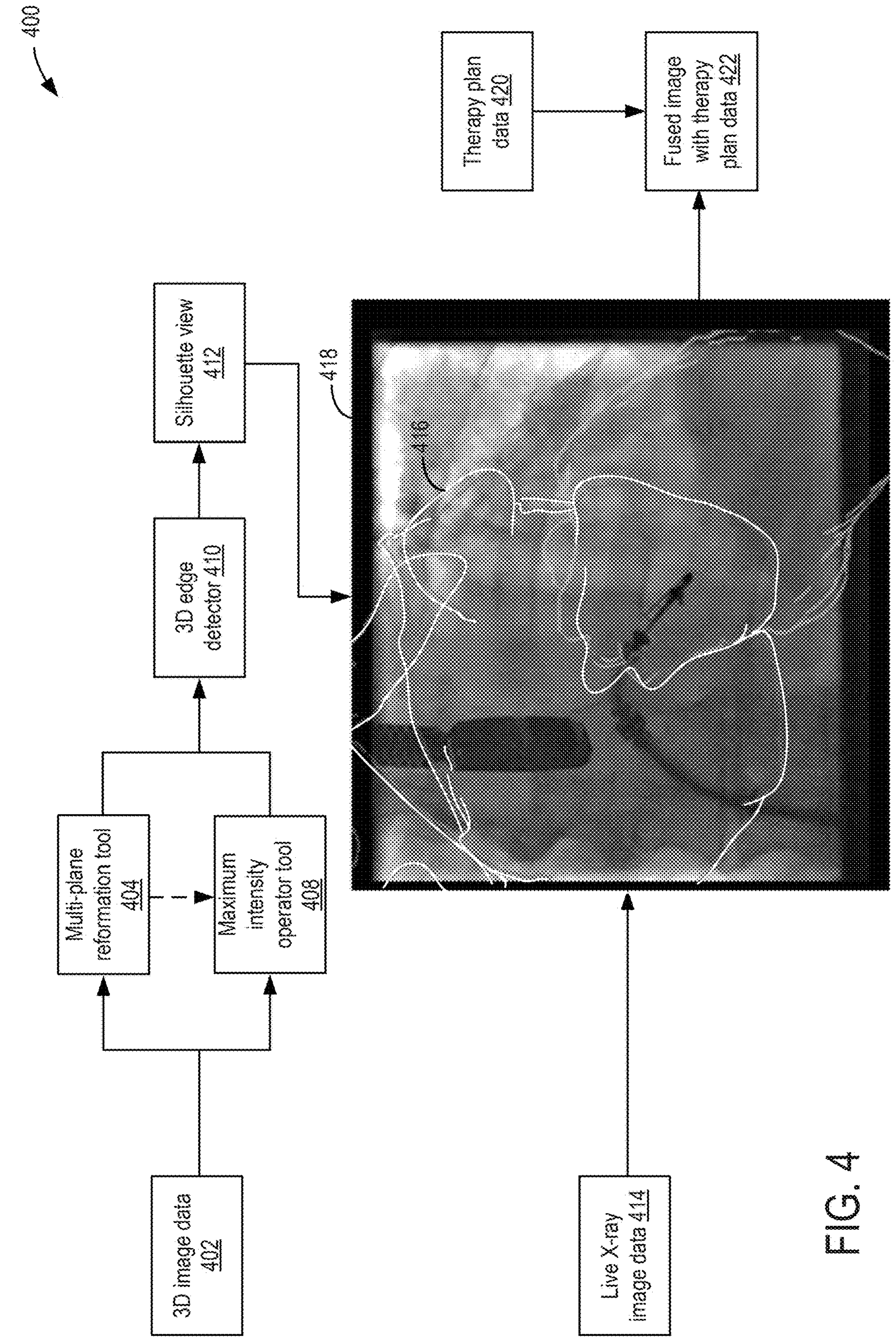
FIG. 4 shows a block diagram of a workflow for generating a fused live image comprising X-ray image data, 3D image data, and therapy plan data, according to an embodiment.
Figure 6:
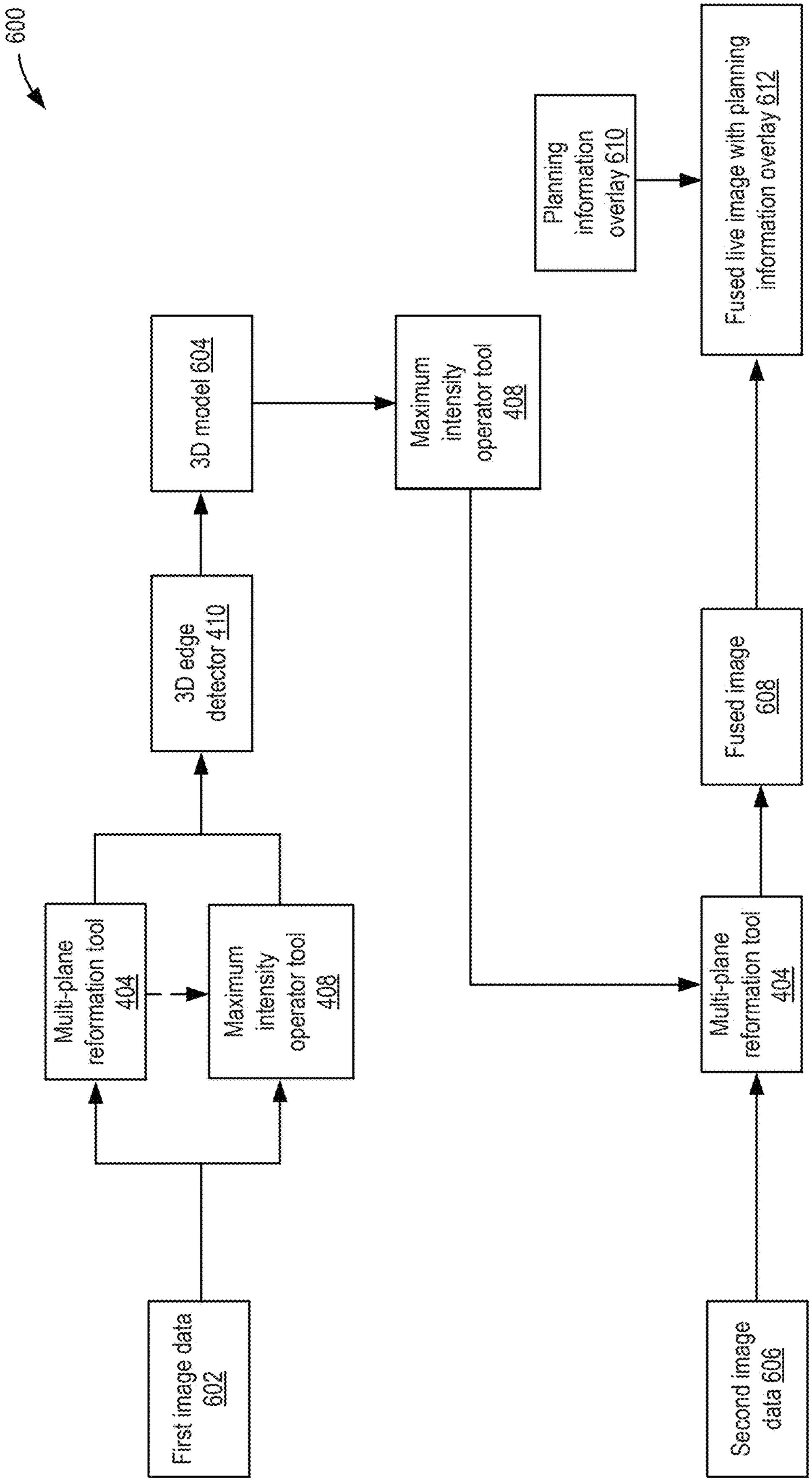
FIG. 6 shows a block diagram of a workflow for generating a fused image comprising a first image data of an anatomical region of interest (ROI), a second image data of the ROI, and a planning information overlay, according to an embodiment.

An example CT imaging system is shown in FIG. 1, where the CT imaging system is configured to capture three-dimensional (3D) views of an imaging subject. FIG. 2 block schematic diagram of an exemplary X-ray imaging system configured to capture live and/or static two-dimensional (2D) views of an imaging subject. FIG. 3 shows a block diagram of an image processing system that is configured to receive image data from different imaging systems, such as a multi-modality imaging system including the CT imaging system of FIG. 1 and/or the X-ray imaging system of FIG. 2. FIGS. 4 and 6 illustrate workflows for generating a single tomographic image that include elements captured by multiple different medical imaging systems.

Figure 5:
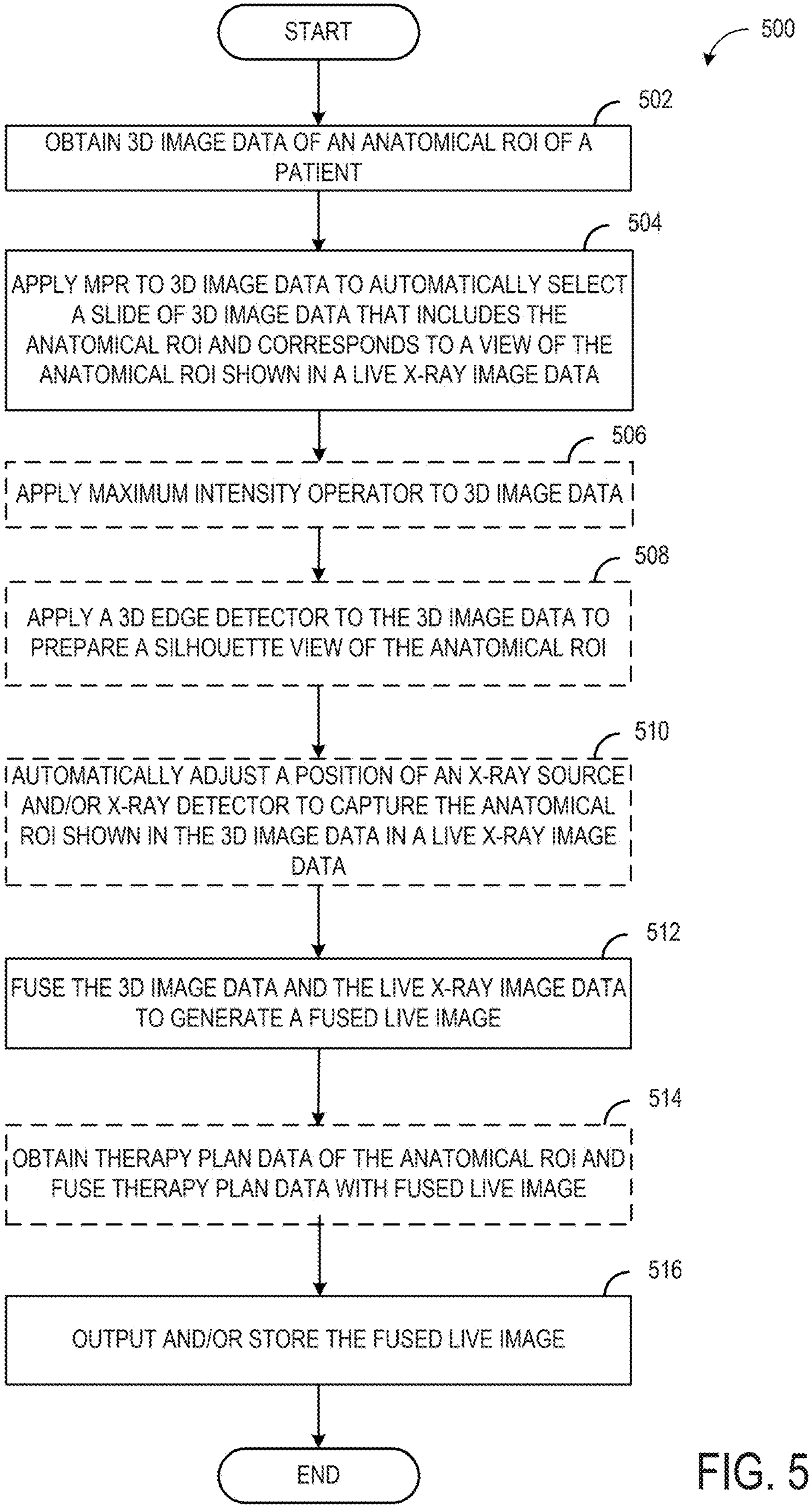
FIG. 5 shows a flow chart for a method for generating a fused live image comprising X-ray image data, 3D image data, and therapy plan data, according to an embodiment.
Figure 7:
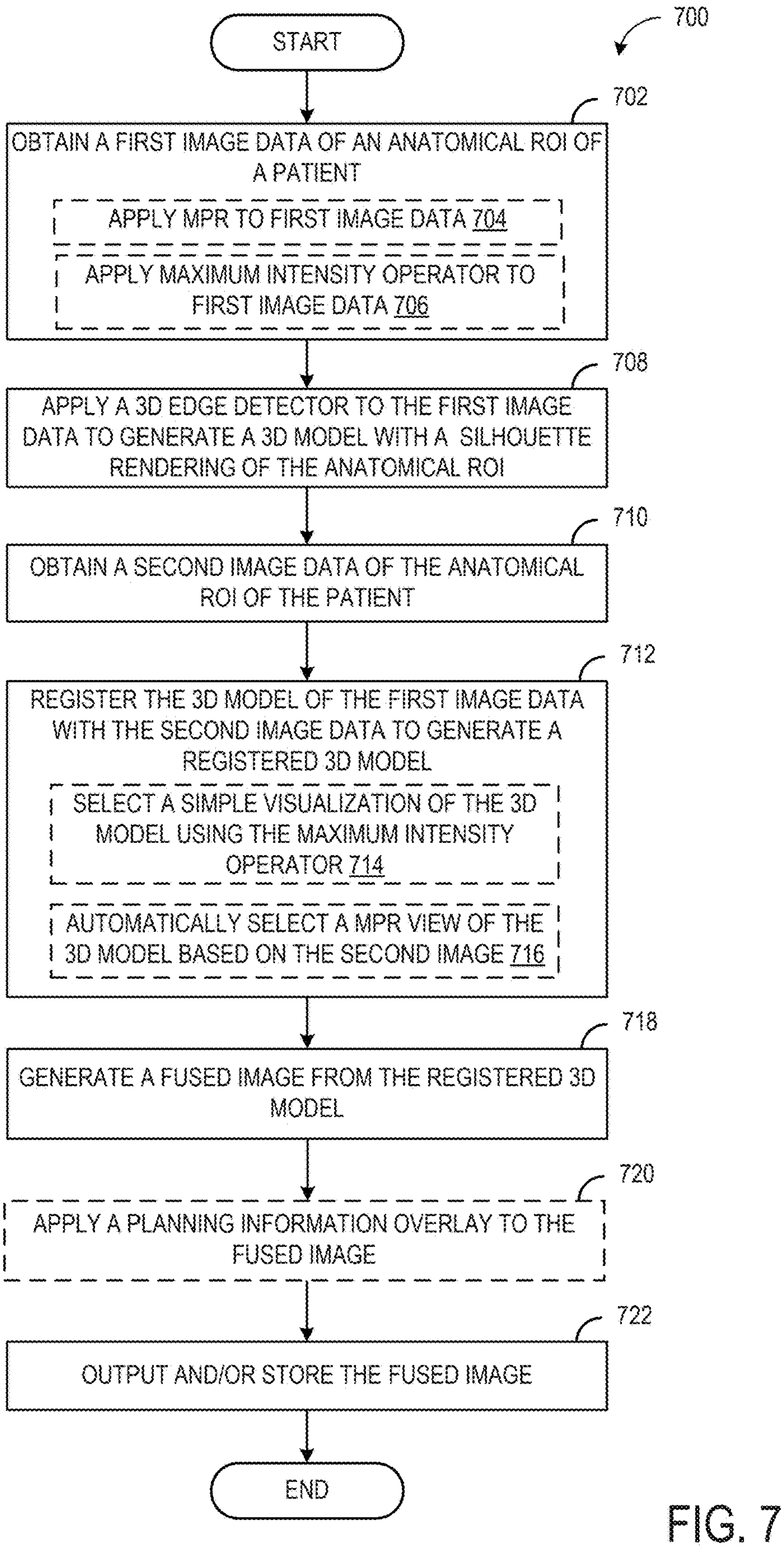
FIG. 7 shows a flow chart for a method for generating a fused image comprising a first image data of a ROI, a second image data of the ROI, and a planning information overlay, according to an embodiment.

FIGS. 5 and 7 show flow charts of methods for executing the workflows shown in FIGS. 4 and 6, respectively. FIGS. 8-12 show example images captured using a CT imaging system and/or an X-ray imaging system, and include example images at various stages of image processing to generate the single tomographic image, as described with respect to the methods of FIGS. 5 and 7. Generation of the single tomographic image may be at least partially adjusted in response to user input via a user interface, an example of which is shown in FIG. 13.

X-ray interventional imaging and, more specifically, augmented imaging, comprises integration of pre-op and/or peri-op 3D images of an imaging subject (e.g., captured using a CT imaging system) for display by overlaying the 3D images onto a live stream of X-ray images. In some examples, imaging data captured using other imaging methods may be additionally or alternatively used with X-ray image data to prepare a single tomographic image. For example, X-ray image data may be fused with image data captured using cone beam computed tomography (CBCT) and/or magnetic resonance imaging (MRI). Conventional technical challenges associated with this integration are related to image registration, including how to identify and compensate for differences in a position of the imaging subject between live X-ray images and 3D images. Additional challenges include selecting, extracting, and displaying relevant information from the 3D images to overlay on the X-ray images. In conventional methods, relevant information included in the 3D images may be selected by preparing slices of CT image data in a 3D viewer. An operator may apply various tools to further prepare CT image data as a 3D image. For example, the various tools may include thresholding, applying a virtual scalpel, and in some cases applying automatic segmentation tools to extract anatomical structures of interest. Application of these or other tools by a user to prepare the 3D image may demand that the user possess detailed knowledge about the tools and/or subject anatomy, which may be beyond knowledge possessed by an operator of the multi-modality imaging system. Additionally, it may be desirable to include an operation for fusing dynamic CT images, such as a sequence of several (e.g., 10) CT images and/or slices corresponding to different phases of a cardiac cycle. Conventional methods used to prepare 3D images, as described above, may be insufficient to achieve this result.

Conventional methods for image integration of X-ray and CT/CBCT/MRI images demand volume preparation with a 3D viewer and/or simple thresholding to segment out a 3D sub volume (e.g., an anatomical region of interest (ROI)) that is fused over the X-ray image. For example, a fluoroscopy image may be combined with a reformatted view from a 3D volume. The 3D volume may be identified, and the fluoroscopy image may be retroprojected onto the 3D volume for image integration. In another example, the fluoroscopy image may be provided with a geometric parameter and a 3D image may be identified that is parallel to an X-ray image.

In further examples, preparation of pre-op CT image data may include processing CT slices to define a therapy plan. The therapy plan may be presented as a simulated prosthesis with a given size, simulated prosthesis position, and orientation in the CT image. In other examples, the therapy plan may additionally or alternatively include a directional line indicating a target, such as a treatment target and/or a simulated incision. For example, in some cardiac procedures, the directional line may indicate a position at which it is desired to perform a transseptal puncture. For interoperability reasons, the therapy plan may be burnt into the CT slices. Loading CT images that include burnt in therapy plan information into a 3D viewer may pose additional challenges to preparing the 3D images using the 3D viewer according to the methods described above.

Described herein are systems and methods for addressing the above challenges in X-ray interventional imaging. Specifically, the methods described herein do not demand preparation of CT image data with a 3D viewer. The methods may be implemented by an X-ray imaging system and a user interface thereof, and enable CT image data or CBCT image data to be immediately displayed. In another example, the methods may be implemented by an image processing system that is configured to receive image data from multiple different imaging systems and/or imaging devices. Traditional segmentation of anatomic structures is abandoned and replaced by a combination of direct display of a multi-plane reformatted view of a 3D model of the ROI, with or without pre-processing, and simple visualization of the 3D model using a maximum intensity operator. This enables a direct viewing of the therapy plan on the X-ray image. The methods described herein further enables integration of dynamic CT models, as the same display configuration may be applied to different cardiac phases. In this way, CT/CBCT image data and dynamic CT images may be integrated in an interventional procedure without disruption of the procedure workflow. Augmented guidance achieved using these methods may result in dose reduction, contrast reduction, and increased precision of therapy delivery.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments multiple X-ray sources and detectors may be employed to project a plurality of X-ray radiation beams 106 for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may receive image data captured by a second imaging device that is different from the CT system 100, and may execute a method for generating a fused image using image data captured by the CT system 100 and image data captured by the second imaging device.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of a radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the radiation beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a 3D rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary X-ray imaging system 200. Some elements of the X-ray imaging system 200 may be similar to the CT system 100 of FIG. 1. Where the CT system 100 of FIG. 1 is configured to capture static 3D images of an imaging subject, the X-ray imaging system 200 is configured to capture live 2D images of the imaging subject. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the X-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters. As further described herein, the operator console 220 may be used to adjust a position of the gantry 102, including a position of the X-ray source 104 and/or the detector array 108, to adjust a region of the subject 112 captured by the imaging system 200.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes described herein may be stored as executable instructions in non-transitory memory on a computing device (or controller) in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

Turning to FIG. 3, a block diagram of an example image processing system 300 is shown. The image processing system 300 may be incorporated into one or more of a multi-modality imaging system, a CT imaging system, an X-ray imaging system, and so on, and/or may be a stand-alone device. For example, the image processing system 300 may be an example of the image reconstructor 230 of FIG. 2, and/or the image processor unit 110 of FIG. 1. In some embodiments, at least a portion of the medical image processing system 300 is disposed at a device (e.g., an edge device or server) communicably coupled to two or more medical imaging systems via wired and/or wireless connections. In some embodiments, the image processing system 300 is disposed at a separate device (e.g., a workstation) that can receive images from the medical imaging systems or from a storage device that stores the images generated by the medical imaging systems. The image processing system 300 may comprise an image processor 331, a user input device 332, and a display device 333. For example, the image processor 331 may be operatively/communicatively coupled to the user input device 332 and the display device 333.

The image processor 331 includes a processor 304 configured to execute machine-readable instructions stored in a non-transitory memory 306. The processor 304 may be single core or multi-core, and the programs executed by the processor 304 may be configured for parallel or distributed processing. In some embodiments, the processor 304 may optionally include individual components that are distributed throughout two or more devices, which may be remotely located and/or configured for coordinated processing. In some embodiments, one or more aspects of the processor 304 may be virtualized and executed by remotely-accessible networked computing devices configured in a cloud computing configuration. In some embodiments, the processor 304 may include other electronic components capable of carrying out processing functions, such as a digital signal processor, a field-programmable gate array (FPGA), or a graphics board. In some embodiments, the processor 304 may include multiple electronic components capable of carrying out processing functions. For example, the processor 304 may include two or more electronic components selected from a plurality of possible electronic components, including a central processor, a digital signal processor, a field-programmable gate array, and a graphics board. In still further embodiments, the processor 304 may be configured as a graphical processing unit (GPU), including parallel computing architecture and parallel processing capabilities.

In the embodiment shown in FIG. 3, the non-transitory memory 306 stores a 3D image module 313 and medical image data 314. The 3D image module 313 includes one or more algorithms to process input medical images from the medical image data 314. In some examples, the 3D module 312 may generate a dynamic 3D CT image from dynamic 3D CT image data. For example, the 3D module 312 may include one or more image recognition algorithms, shape or edge detection algorithms, gradient algorithms, and the like to process the 3D ultrasound image data. Additionally or alternatively, the 3D module 312 may store instructions for implementing a neural network, such as a convolutional neural network, for detecting anatomical ROIs captured in the medical image data 314 in real-time. For example, the 3D module 312 may include trained and/or untrained neural networks and may further include training routines, or parameters (e.g., weights and biases), associated with one or more neural network models stored therein. A 3D edge detector may be stored in the 3D module 312, where the 3D edge detector is configured to prepare a silhouette view of an anatomical ROI captured in medical image data 314. For example, the 3D edge detector may be a trained deep learning and/or artificial intelligence model that is configured to automatically identify one or more anatomical structures and generating an outline of the one or more anatomical structures. The 3D edge detector may compare a size, shape, and other characteristics of anatomies in the image data with characteristics of defined anatomies. For example, the 3D edge detector may identify a morphology present in the image data as a structure of a heart by comparing the image data to defined anatomies. The 3D edge detector may then generate an outline of the heart anatomy shown in the image data using the image data and referencing the defined heart anatomy used to train the 3D edge detector. In some embodiments, the 3D module 312 may evaluate the medical image data 314 as it is acquired in real-time. Additionally or alternatively, the 3D image module 313 may evaluate the medical image data 314 offline, not in real-time.

Optionally, the image processor 331 may be communicatively coupled to a training module 310, which includes instructions for training one or more of the machine learning models stored in the 3D image module 313. The training module 310 may include instructions that, when executed by a processor, cause the processor to build a model (e.g., a mathematical model) based on sample data to make predictions or decisions regarding the detection and classification of anatomical irregularities without the explicit programming of a conventional algorithm that does not utilize machine learning. In one example, the training module 310 includes instructions for receiving training data sets from the medical image data 314. The training data sets comprise sets of medical images, associated ground truth labels/images, and associated model outputs for use in training one or more of the machine learning models stored in the 3D image module 313. The training module 310 may receive medical images, associated ground truth labels/images, and associated model outputs for use in training the one or more machine learning models from sources other than the medical image data 314, such as other image processing systems, the cloud, etc. In some embodiments, one or more aspects of the training module 310 may include remotely-accessible networked storage devices configured in a cloud computing configuration. Further, in some embodiments, the training module 310 is included in the non-transitory memory 306. Additionally or alternatively, in some embodiments, the training module 310 may be used to generate the 3D module 312 offline and remote from the image processing system 300. In such embodiments, the training module 310 may not be included in the image processing system 300 but may generate data stored in the image processing system 300. For example, the 3D module 312 may be pre-trained with the training module 310 at a place of manufacture.

The non-transitory memory 306 further stores the medical image data 314. The medical image data 314 includes, for example, functional and/or anatomical images captured by an imaging modality, such as an ultrasound imaging system, an MRI system, a CT system, a PET system, an X-ray system, etc. As one example, the medical image data 314 may include 3D CT images and live 2D X-ray images. Further, the medical image data 314 may include one or more of 3D images, 3D images, static single frame images, and multi-frame cine-loops (e.g., movies) captured using other medical imaging modalities.

In some embodiments, the non-transitory memory 306 may include components disposed at two or more devices, which may be remotely located and/or configured for coordinated processing. In some embodiments, one or more aspects of the non-transitory memory 306 may include remotely-accessible networked storage devices in a cloud computing configuration. As one example, the non-transitory memory 306 may be part of a PACS that is configured to store patient medical histories, imaging data, test results, diagnosis information, management information, and/or scheduling information, for example.

The image processing system 300 may further include the user input device 332. The user input device 332 may comprise one or more of a touchscreen, a keyboard, a mouse, a trackpad, a motion sensing camera, or other device configured to enable a user to interact with and manipulate data stored within the image processor 331.

The display device 333 may include one or more display devices utilizing any type of display technology. In some embodiments, the display device 333 may comprise a computer monitor and may display unprocessed images, processed images, parametric maps, and/or exam reports. The display device 333 may be combined with the processor 304, the non-transitory memory 306, and/or the user input device 332 in a shared enclosure or may be a peripheral display device. The display device 333 may include a monitor, a touchscreen, a projector, or another type of display device, which may enable a user to view medical images and/or interact with various data stored in the non-transitory memory 306. In some embodiments, the display device 333 may be included in a smartphone, a tablet, a smartwatch, or the like.

It may be understood that the image processing system 300 shown in FIG. 3 is one non-limiting embodiment of an image processing system, and other imaging processing systems may include more, fewer, or different components without departing from the scope of this disclosure. Further, in some embodiments, at least portions of the image processing system 300 may be included in the CT system 100 of FIG. 1 and/or the imaging system 200 of FIG. 2, or vice versa (e.g., at least portions of the CT system 100 and/or the imaging system 200 may be included in the image processing system 300).

Turning to FIG. 4, a workflow 400 is shown for generating a fused live image comprising X-ray image data, 3D image data, and therapy plan data. The workflow 400 may be executed by an X-ray imaging system, such as the X-ray imaging system 200 of FIG. 2. Briefly, the workflow 400 includes: obtaining 3D image data of an anatomical region of interest (ROI) of an imaging subject (e.g., a patient); obtaining live X-ray image data capturing the anatomical ROI of the imaging subject; processing the 3D image data and the live X-ray image data, and fusing processed 3D image data, live X-ray image data, and therapy plan data to generate a fused live image that includes elements of each data source. In this way, a single tomographic image is generated that includes image elements captured using different imaging modalities. The single tomographic image is generated without applying a 3D viewer to 3D image data captured by a CT imaging system (e.g., the CT system of FIG. 1). The workflow 400 may include real-time adjustment of X-ray source and/or X-ray detector elements to adjust the live X-ray image data, which may enable registration of CT imaging data captured prior to capture of the live X-ray image data to the live X-ray image data.

The workflow 400 includes acquiring 3D image data 402 of an anatomical ROI of a patient. The 3D image data 402 may be captured by a 3D imaging system, such as a CT system. The X-ray imaging system executing the workflow 400 is communicably coupled to the CT system configured to capture the 3D image data 402. For example, the X-ray imaging system may be directly communicably coupled to the CT system (e.g., via a wired and/or a wireless connection). In another example, the X-ray imaging system may be indirectly coupled to the CT system, where the CT system and the X-ray imaging system are both communicably coupled to a database or other device configured to receive, store, and output 3D image data 402.

In some examples, the 3D image data 402 may be processed using one or more tools to identify a desired view of the anatomical ROI. The desired view of the anatomical ROI may be automatically identified by the workflow 400. For example, the X-ray imaging system may include a trained machine learning model and/or artificial intelligence model configured to identify anatomical structures in 3D image data, and determine if the anatomical structure is captured in its entirety in a FOV of the 3D image data. A multi-plane reformation (MPR) tool 404 may be applied to the 3D image data 402 to select a MPR visualization of the anatomical ROI. The MPR tool 404 may be stored in a memory of the X-ray imaging system executing the workflow 400, such as in a memory of the computing device 216 of FIG. 2. The MPR tool 404 may convert one or more elements of the 3D image data 402 from a first plane to a second plane, different from the first plane, to provide a desired view of the anatomical ROI. For example, the 3D image data 402 may be acquired in an axial plane, and converted by the MPR tool 404 to a non-axial plane (e.g., coronal, sagittal, oblique). Further, a slice of the 3D image data may be automatically selected by the MPR tool based on a position of an x-ray source and/or an x-ray detector of an x-ray imaging system.

A maximum intensity operator tool 408 may be applied to the 3D image data 402 to select a view of the 3D image data 402 that displays the anatomical ROI at a maximum intensity, relative to other views of the anatomical ROI included in the 3D image data 402. In some examples, the maximum intensity operator tool 408 may be applied to the MPR visualization identified using the MPR tool 404. The maximum intensity operator 408 may be stored in the memory of the X-ray imaging system executing the workflow 400. Application of the maximum intensity operator 408 to the 3D image data 402 generates a maximum intensity projection (MIP), which may be presented (e.g., displayed) and/or stored as a series of 2D images generated form the 3D image data 402.

The MPR visualization of the 3D image data 402 and/or the MIP of the 3D image data 402 may be selected in response to user input in some embodiments. Referring briefly to FIG. 13, an example user interface 1300 is shown that may be used to adjust a view of the 3D image data. Visualization of different MPR at different depths may be selected, where the different depths correspond to given configurations of an X-ray imaging chain. Additionally or alternatively, a maximum intensity level of the 3D image data 402 may be selected via the user interface. In the example user interface 1300, sliders 1302 and push buttons 1304 may be provided to enable adjustment of the MPR visualization. For example, the sliders 1302 may be used to adjust a depth of cut shown in the MPR visualization, as well as a frame and a position of the cut. A geometrical plane that is parallel to a FOV captured by the x-ray image detector and a depth of the MPR visualization may be defined in response to a user input via the user interface 1300. For example, an anatomical content shown in the MPR may be visualized by a user and/or automatically identified by a trained machine learning algorithm, and the geometrical plane and/or depth of the MPR may be adjusted to include desired anatomical content (e.g., the anatomical ROI). Push buttons 1304 may be used to adjust a zoom level of the MPR visualization. Sliders 1302 may further be used to adjust an opacity and/or a brightness of the image data. Further, the push buttons 1304 may be configured with preset intensity and/or MPR framing values that may be automatically applied to the 3D image data in response to selection of the corresponding push button 1304. The user interface 1300 may be included in a tactile user device, such as the display 232 of FIG. 2.

Returning to FIG. 4, a 3D edge detector 410 is optionally applied to the 3D image data 402 to generate a silhouette view 412 of the anatomical ROI. In examples where the MPR tool 404 and/or the maximum intensity operator 408 are applied to the 3D image data 402, the 3D edge detector 410 is applied to the MPR visualization and/or the MIP. The 3D edge detector 410 may be stored in the memory of the X-ray imaging system executing the workflow 400. The 3D edge detector 410 may be an automated tool, such as a trained deep learning and/or artificial intelligence model, that is configured to automatically identify one or more anatomical structures and generate an outline of the one or more anatomical structures. The outline may be shown as a colored and/or highlighted line around a perimeter of the anatomical structure(s). The silhouette view 412 generated by the 3D edge detector 410 includes an outline 416 of the anatomical ROI, as shown in a fused image 418.

The workflow 400 further includes acquiring live X-ray image data 414. The live X-ray image data 414 may be acquired using a second imaging system that is different from the first imaging system used to acquire the 3D image data 402. For example, the second imaging system is an X-ray imaging system. The live X-ray image data 414 is 2D image data of the same imaging subject captured in the 3D image data 402. The live X-ray image data 414 may or may not include at least some of the anatomical ROI captured by the 3D image data 402. The live X-ray image data 414 is to be fused with the 3D image data 402 to form a fused image that includes elements of the live X-ray image data 414 and the 3D image data 402. Prior to fusing the image data, a method may include adjusting a position of an X-ray detector and/or an X-ray source of the X-ray imaging system used to capture the live X-ray image data 414. For example, the live X-ray image data 414 may be captured and processed according to the workflow 400 in real time (e.g., processed as the data is captured using the X-ray imaging system). The FOV of the X-ray imaging system (e.g., a region captured by the X-ray imaging system) may be adjusted by adjusting one or more of a position of the X-ray detector and/or the X-ray source. The FOV of the live X-ray image data 414 is adjusted to include the same view of the anatomical ROI of the imaging subject that is shown in the 3D image data 402.

The silhouette view 412 of the anatomical ROI is fused with the live X-ray image data 414 to generate a fused image 418. In this way, elements of the anatomical ROI captured by the different imaging systems are presented in a single tomographic view. As the 3D image data 402 is captured prior to or during an operation (e.g., surgical procedure) that precedes capture of the live X-ray image data 414, the fused image 418 shows image data captured at different times in a single image. For example, the static 3D image data is fused with live X-ray image data 414. This may reduce complexity of image data preparation, as the 3D image data is not processed using a 3D image viewer prior to being output for display. Instead, the 3D image data is registered with the live X-ray image data to show different elements of the same anatomical ROI in a single view. This may simplify display, as desired image information is displayed in a single image and does not demand selection and navigation among multiple screens, files, and/or images to identify the anatomical ROI.

In some examples, the workflow 400 further includes fusing therapy plan data 420 with the fused image 418 to generate a fused image with therapy plan data 422. The therapy plan data 420 may include a simulated prosthesis with a given size, simulated prosthesis position, and orientation positioned relative to a static image (e.g., the 3D image data 402) and/or a dynamic image (e.g., the live X-ray image data 414). The therapy plan 420 may additionally or alternatively include a directional line indicating a target, such as a treatment target, and/or a simulated incision. In some examples, the therapy plan data 420 may be presented as an overlay that is not fused or otherwise coupled to the 3D image data 402. In this way, a single image is generated that includes 3D image data 402, live X-ray image data 414, and the therapy plan data 420.

Turning to FIG. 5, a method 500 is shown for generating a fused image comprising 3D image data and live X-ray image data. The method 500 may be implemented an X-ray imaging system, such as the X-ray imaging system 200 of FIG. 2. The method 500 is described herein with reference to FIGS. 1-3, and may be adapted to other imaging modalities. Briefly, instructions for executing the method 500 may be stored as executable instructions in non-transitory memory and executed by a processor. Further, in some embodiments, the method 500 is performed in real-time (e.g., as live X-ray image is captured). The method 500 may be an example of the workflow 400 of FIG. 4.

At 502, the method 500 includes obtaining 3D image data of an anatomical ROI of a patient. The 3D image data may be captured by a CT imaging system, such as the CT system 100 of FIG. 1. The 3D image data includes an anatomical ROI of a patient in multiple views that are conventional to a 3D image captured by a conventional CT imaging system. The X-ray imaging system executing the method 500 may be communicably coupled to the CT imaging system used to capture the 3D image data, and/or may be communicably coupled to a database that is in turn communicably coupled to the CT imaging system and is configured to store and output 3D image data, as described with respect to FIG. 4.

At 504, the method 500 includes applying multi-planar reformatting to the 3D image data. A MPR tool may be applied to the 3D image data to select a MPR visualization of the anatomical ROI. The MPR tool may convert one or more elements of the 3D image data from a first plane to a second plane, different from the first plane, to provide a desired view of the anatomical ROI.

At 506, the method 500 optionally includes applying a maximum intensity operator to the 3D image data. A maximum intensity operator tool may be applied to the 3D image data to select a view of the 3D image data that displays the anatomical ROI at a maximum intensity, relative to other views of the anatomical ROI included in the 3D image data. In some examples, the maximum intensity operator tool may be applied to the MPR visualization selected at operation 504.

In conventional methods for processing 3D image data to be fused with image data acquired from different imaging systems, the 3D image data may be processed using a 3D image viewer. In some examples, the method 500 may include processing the 3D image data with a 3D image viewer to identify the anatomical ROI via 3D image segmentation. However, by excluding the 3D image segmentation operation and processing the 3D image data with respect to the live X-ray image data using multi-planar reformatting (e.g., the multi-plane reformation tool), the maximum intensity operator tool, and adjustment of the FOV of the X-ray imaging system by adjusting one or more of the X-ray source and the X-ray detector, a processing demand and memory demand may be decreased. This may further increase a processing speed and decrease a complexity of the operation, compared to conventional methods that use the 3D image viewer.

At 508, the method 500 optionally includes applying a 3D edge detector to the 3D image data to prepare a silhouette view of the anatomical ROI present in the 3D image data. The 3D edge detector may identify structures and generate an outline of the anatomical ROI.

At 510, the method 500 includes automatically adjusting a position of an X-ray source and/or of an X-ray detector to capture the anatomical ROI in a live X-ray image. A FOV captured by the X-ray imaging system may be compared to the silhouette view of the anatomical ROI to determine if the anatomical ROI is captured by the X-ray imaging system. If the anatomical ROI is not shown in the FOV of the X-ray imaging system, the FOV may be adjusted to enable visualization of the anatomical ROI. For example, the gantry of the X-ray imaging system may be rotated, the table on which the imaging subject is positioned may be moved, and so on to adjust the FOV captured.

At 512, the method 500 includes fusing the 3D image data and the live X-ray image data to generate a fused image. The 3D image data and the live X-ray image data may be registered by aligning the anatomical ROI in each of the image data. In examples of the method 500 where the silhouette view is prepared, the 3D image data and the live X-ray image data may be automatically fused using the silhouette view. In other examples, the 3D image data and the live X-ray image data may be aligned via a user input. For example, an operator may select and move a display of the X-ray image data over a display of the 3D image data (or vice-versa) to superimpose a common anatomical structure of interest (e.g., the anatomical ROI) that has been identified, either visually by the user and/or by the processor, using methods described herein. The X-ray image data and the 3D image data are combined by a pixel-by-pixel combination. The two image data may be combined using an adjustable coefficient that represents an opacity of each image data with respect to the other. The adjustable coefficient may be adjusted via the user interface described with respect to FIG. 13. For example, a coefficient of the X-ray image data may be increased to increase an opacity of the X-ray image data, and thus elements of the X-ray image data may be more opaque in the fused image, enabling elements of the 3D image data to be more visible in the fused live image. The fused live image may in this way be generated without preparation using a 3D viewer. In some examples, one or more steps other than the image fusion step of the method 500 and other methods described herein may prepare a model of the 3D image data using the 3D viewer. Fusing the 3D image data and the X-ray image data enables content of both image to be perceived in the resulting fused live image.

At 514, the method 500 optionally includes obtaining therapy plan data of the anatomical ROI, and fusing the therapy plan data with the fused image. The therapy plan data may include a silhouette view of the anatomical ROI, coordinates that correspond to the FOV of the live X-ray image, and/or other markers that indicate a relative positioning of elements of the therapy plan with respect to the anatomical ROI. The therapy plan data may be fused with the fused image using a similar method for fusing the live X-ray image data and the 3D image data.

At 516, the method 500 includes outputting and/or storing the fused image. For example, the fused live image (e.g., optionally including the therapy plan data) may be output for display on a display device of the X-ray imaging system. The method 500 ends.

Turning to FIG. 6, a workflow 600 is shown for generating a fused live image comprising X-ray image data, 3D image data, and a planning information overlay. The workflow 600 includes some of the same elements of the workflow 400. These elements have the same numbering and will not be reintroduced, for brevity. The workflow 600 may be executed by an image processing device system, such as the image processing system 300 of FIG. 3. Briefly, the workflow 600 includes: obtaining a first set of image data of an anatomical region of interest (ROI) of an imaging subject (e.g., a patient) captured using a first imaging system; obtaining a second set of image data capturing the anatomical ROI of the imaging subject using a second imaging system, different from the first imaging system; processing the first set of image data and the second set of image data; and fusing processed image data and a planning information overlay to generate a fused live image that includes elements of each data source. In this way, a single tomographic image is generated that includes image elements captured using different imaging modalities.

The workflow 600 includes acquiring a first image data 602 of an anatomical ROI of a patient. The first image data 602 may be captured by a 3D imaging system, such as a CT system, and may be equivalent to the 3D image data 402 of FIG. 4. In other examples, the first image data 602 may be a different type of 3D image data. The image processing system executing the workflow 600 is communicably coupled to the imaging system configured to capture the first image data 602. For example, the image processing system may be directly communicably coupled to the CT system 100 (e.g., via a wired and/or a wireless connection). In another example, the image processing system may be indirectly coupled to the CT system, where the CT system and the image processing system are both communicably coupled to a database or other device configured to receive, store, and output the first image data 602.

In some examples, the first image data 602 may be processed using one or more tools to identify a desired view of the anatomical ROI. For example, the MPR tool 404 may be applied to the first image data to select a MPR visualization of the anatomical ROI. The maximum intensity operator tool 408 may be applied to the first image data 602 to select a view of the first image data 402 that displays the anatomical ROI at a maximum intensity, relative to other views of the anatomical ROI included in the first image data 602. In some examples, the maximum intensity operator tool 408 may be applied to the MPR visualization. The MPR tool 404 and/or the maximum intensity operator tool 408 may be stored in the memory of the image processing system executing the workflow 600, such as in the 3D module 312 of the image processing system 300 of FIG. 3.

The 3D edge detector 410 is applied to the first image data 602 to generate a 3D model 604 with a silhouette rendering of the anatomical ROI. In examples where the MPR tool 404 and/or the maximum intensity operator 408 are applied to the first image data 602, the 3D edge detector 410 is applied to the MPR visualization and/or the MIP generated by the MPR tool 404 and/or the maximum intensity operator tool 408, respectively. Similar to the silhouette view 412 generated according to the workflow 400, the 3D model 604 may include an outlined view of the anatomical ROI.

The maximum intensity operator tool 408 may be applied to the 3D model 604 with the silhouette rendering of the anatomical ROI to generate a simplified visualization of the anatomical ROI using the first image data 602. The simplified visualization may include identification of pixels within the anatomical ROI (e.g., within the outline of the silhouette of the anatomical ROI) having a maximum intensity of the pixels in the 3D model 604.

The workflow 600 further includes acquiring a second image data 606 of the anatomical ROI of the patient. The second image data 606 is acquired using a second imaging system that is different from the first imaging system used to acquire the first image data 602. For example, the second imaging system is an X-ray imaging system, and the second image data 606 is live X-ray image data. The second image data 606 may or may not include at least some of the anatomical ROI captured in a FOV of the first image data 602.

Whereas the workflow 400 and the method 500 may be implemented by an X-ray imaging system and a position of the X-ray sensor and/or the X-ray detector is adjusted to register the live X-ray image data with the 3D image data, in the workflow 600 and the method 700 further described herein, a MPR view of the 3D model 604 is automatically selected by the image processing system based on the anatomical ROI shown in the second image data 606. For example, the workflow 600 may implement a trained machine learning model and/or artificial intelligence model configured to compare a size, shape, and other characteristics of anatomies in the image data (e.g., the second image data) with defined anatomies and/or with anatomies present in other image data (e.g., the first image data). In the event that the same anatomical ROI is not shown in the first image data and the second image data, the workflow 600 may parse through slices and/or views of the first image data using the MPR tool 404 to identify a view (e.g., a MPR view of the 3D model 604) that shows the anatomical ROI shown in the second image data 606.

The selected MPR view of the 3D model 604 is registered with the second image data 606 to generate a fused image 608. The MPR view of the 3D model 604 and the second image data 606 may be registered using conventional image registration methods that spatially align the image datasets. In this way, elements of the anatomical ROI captured by the different imaging systems are presented in a single tomographic view. This may reduce complexity of image data preparation, as the 3D image data is not processed using a 3D image viewer prior to being output for display. Instead, the 3D image data is registered with the live X-ray image data to show different elements of the same anatomical ROI in a single view. This may simplify display, as desired image information is displayed in a single image and does not demand selection and navigation among multiple screens, files, and/or images to identify the anatomical ROI. Additionally, this may reduce user and/or imaging subject exposure to radiation, as well as decrease time and resource demands of imaging, as the workflow 600 does not include adjustment of the X-ray imaging system to adjust the FOV captured by the X-ray imaging system.

In some examples, the workflow 600 further includes fusing a planning information overlay 610 with the fused image 608 to generate a fused image with planning information overlay 612. The planning information overlay 610 may be similar to the therapy plan 420 of FIG. 4, and may include a simulated prosthesis with a given size, position, and orientation in the first image data 602 and/or the second image data 606. The planning information overlay 610 may additionally or alternatively include a directional line indicating a target, such as a treatment target.

Turning to FIG. 7, a method 700 is shown for generating a fused image comprising a first image data captured using a first imaging system, and a second image data captured using a second imaging system that is different from the first imaging system. The first imaging data may be static, 3D image data, and the second image data may be dynamic, 2D image data. The method 700 may be implemented an image processing system, such as the image processing system 300 of FIG. 3. The method 700 is described herein with reference to FIGS. 1-3, and may be adapted to other imaging modalities. Briefly, instructions for executing the method 700 may be stored as executable instructions in non-transitory memory (e.g., the non-transitory memory 306) and executed by a processor (e.g., the processor 304). Further, in some embodiments, the method 700 is performed in real-time (e.g., as dynamic image data is captured). The method 700 may be an example of the workflow 600 of FIG. 6.

At 702, the method 700 includes obtaining the first image data of an anatomical ROI of a patient. The first image data may be captured by a first imaging system. The first imaging system may be a CT imaging system, such as the CT system 100 of FIG. 1. The first image data includes an anatomical ROI of a patient in multiple views that are conventional to a 3D image captured by a conventional 3D imaging system. The image processing system executing the method 700 may be communicably coupled to the first imaging system used to capture the first image data, and/or may be communicably coupled to a database that is in turn communicably coupled to the first imaging system and is configured to store and output the first image data, as described with respect to FIG. 6.

At 704, the method 700 optionally includes applying multi-planar reformatting to the first image data. A MPR tool may be applied to the first image data to select a MPR visualization of the anatomical ROI. The MPR tool may convert one or more elements of the first image data from a first plane to a second plane, different from the first plane, to provide a desired view of the anatomical ROI.

At 706, the method 700 optionally includes applying a maximum intensity operator to the first image data. A maximum intensity operator tool may be applied to the first image data to select a view of the first image data that displays the anatomical ROI at a maximum intensity, relative to other views of the anatomical ROI included in the first image data. In some examples, the maximum intensity operator tool may be applied to the MPR visualization selected at operation 704.

In conventional methods for processing a first image data to be fused with image data acquired from different imaging systems, the first image data may be processed using a 3D image viewer. In some examples, the method 700 may include processing the first image data with a 3D image viewer to identify the anatomical ROI via 3D image segmentation. However, by excluding the 3D image segmentation operation and processing the first image data with respect to the second image data using multi-planar reformatting, the maximum intensity operator tool, and automatic selection of a MPR view of the 3D model of the first image data, based on the second image data, a processing demand and memory demand may be decreased. This may further increase a processing speed and decrease a complexity of the operation, compared to conventional methods that use the 3D image viewer.

At 708, the method 700 includes applying a 3D edge detector to the first image data to prepare a silhouette view of the anatomical ROI present in the first image data. The first edge detection tool may identify structures and generate an outline of the anatomical ROI.

At 710, the method 700 includes obtaining a second image data of the anatomical ROI of the patient. The second image data may be captured by a second imaging system. The second imaging system may be an X-ray imaging system, such as the X-ray imaging system 200 of FIG. 2. The second image data includes an anatomical ROI of a patient in a live (e.g., dynamic) view. The image processing system executing the method 700 may be communicably coupled to the second imaging system used to capture the second image data in such a way that the method 700 is executed using the live data.

At 712, the method 700 includes registering a 3D model of the first image data with the second image data to generate a registered 3D model (e.g., the 3D model 604 of the workflow 600). Generating the registered 3D model may include, at 714, applying the maximum intensity operator tool to the 3D model of the first image data to generate a simplified visualization of the anatomical ROI using the first image data. The simplified visualization may include identification of pixels within the anatomical ROI (e.g., within the outline of the silhouette of the anatomical ROI) having a maximum intensity of the pixels in the 3D model.

Generating the registered 3D model may further include, at 716, automatically selecting a MPR view of the 3D model of the first image data based on the anatomical ROI shown in the second image data. For example, the method 700 may parse through slices and/or views of the first image data using the MPR tool to identify a view (e.g., a MPR view of the 3D model) that shows the anatomical ROI shown in the second image data.

At 718, the method 700 includes generating a fused image from the registered 3D model of the selected MPR view of the 3D model and the second image data. In this way, elements of the anatomical ROI captured by the different imaging systems are presented in a single tomographic view. This may reduce complexity of image data preparation, as the first image data and the second image data are not processed using a 3D image viewer prior to being output for display. The first image data is registered with the second image data in real time (e.g., corresponding with the dynamic/live second image data). This may simplify display, as desired image information is displayed in a single image and does not demand selection and navigation among multiple screens, files, and/or images to identify the anatomical ROI.

The method 700 optionally includes, at 720, applying a planning information overlay to the fused image. The planning information overlay may be fused with the fused image and/or overlaid on the fused image for display.

At 722, the method 700 includes outputting and/or storing the fused image. For example, the fused live image (e.g., optionally including the planned information overlay) may be output for display on a display device of the image processor (e.g., the display device 333). The method 700 ends.

Turning to FIGS. 8-12, example fused images are shown, including fused images generated by fusing a first image data (e.g., 3D image data) and a second image data (e.g., live X-ray image data). As described with respect to FIGS. 4-7, the 3D image data is processed to acquire an outlined, silhouette view of the anatomical ROI. The silhouette view is shown in some of the fused images of FIGS. 8-12. Additionally, the fused image may include planning information and/or a therapy plan overlaid on and/or fused with the fused image. One or more of the fused images of FIGS. 8-12 may be output for display on a display device and/or stored in a memory (e.g., of the X-ray imaging system 200 and/or the image processing system 300).

Figure 8:
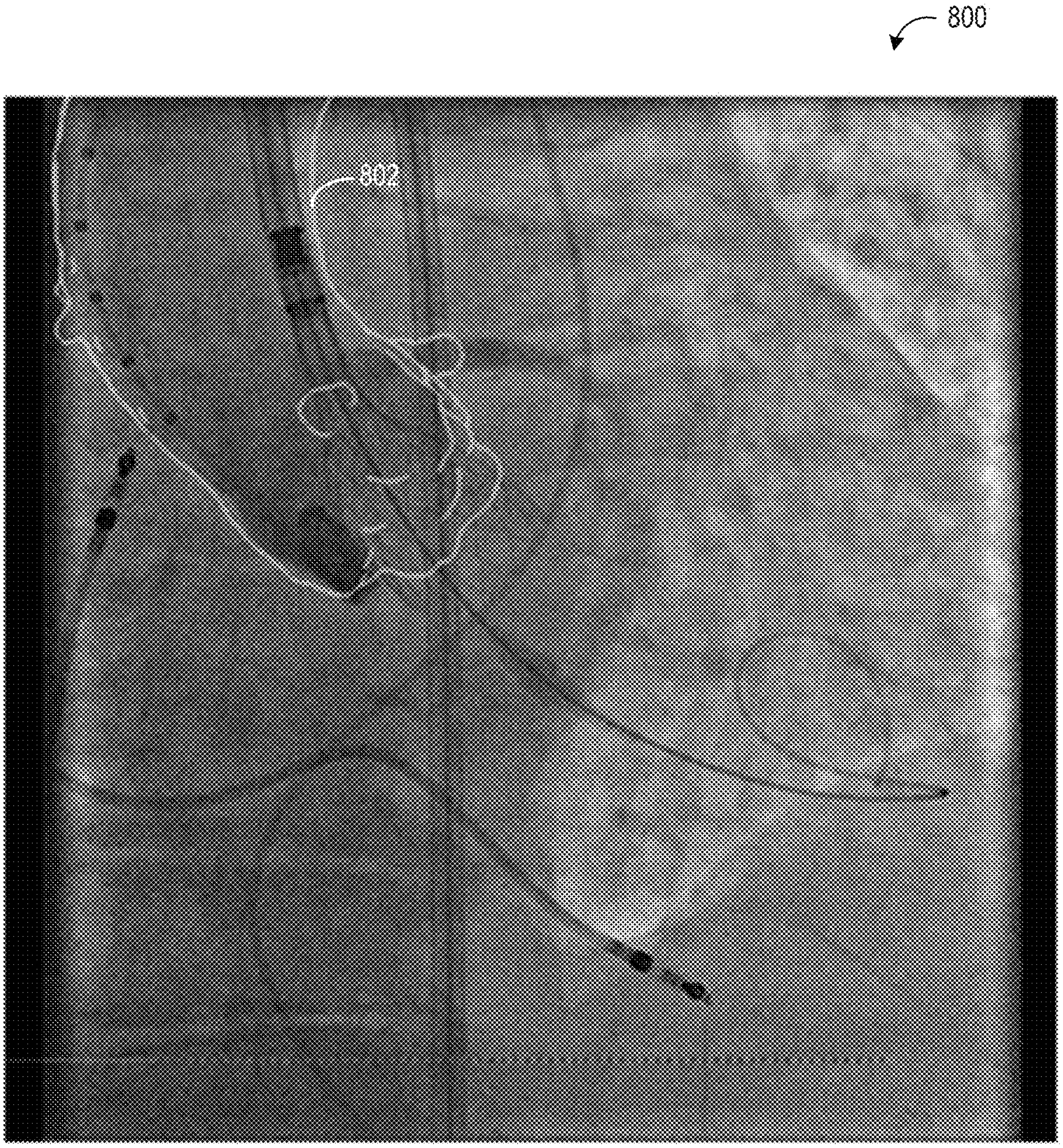
FIG. 8 shows an example fused image of a left aorta with a segmented model.

FIG. 8 shows a first fused image 800. The first fused image 800 may be generated by fusing live X-ray image data and segmented 3D image data, as described with respect to FIGS. 4-7. For example, the first fused image 800 shows segmentation of a left aorta 802 of a patient, which may be shown as an outline provided in a silhouette view of the 3D image data. The methods 500 and 700 may register 3D image data and live X-ray image data to generate the first fused image 800 according to standard methods used to fuse segmented models. The resulting first fused image 800 provides visualization of a structure (e.g., the left aorta) that may itself not be segmented, and is instead shown in the silhouette view. This may reduce processing demand, as well as memory storage demand and network traffic demand to send, receive, and process (e.g., segment) multiple images prior to image registration.

Figure 9:
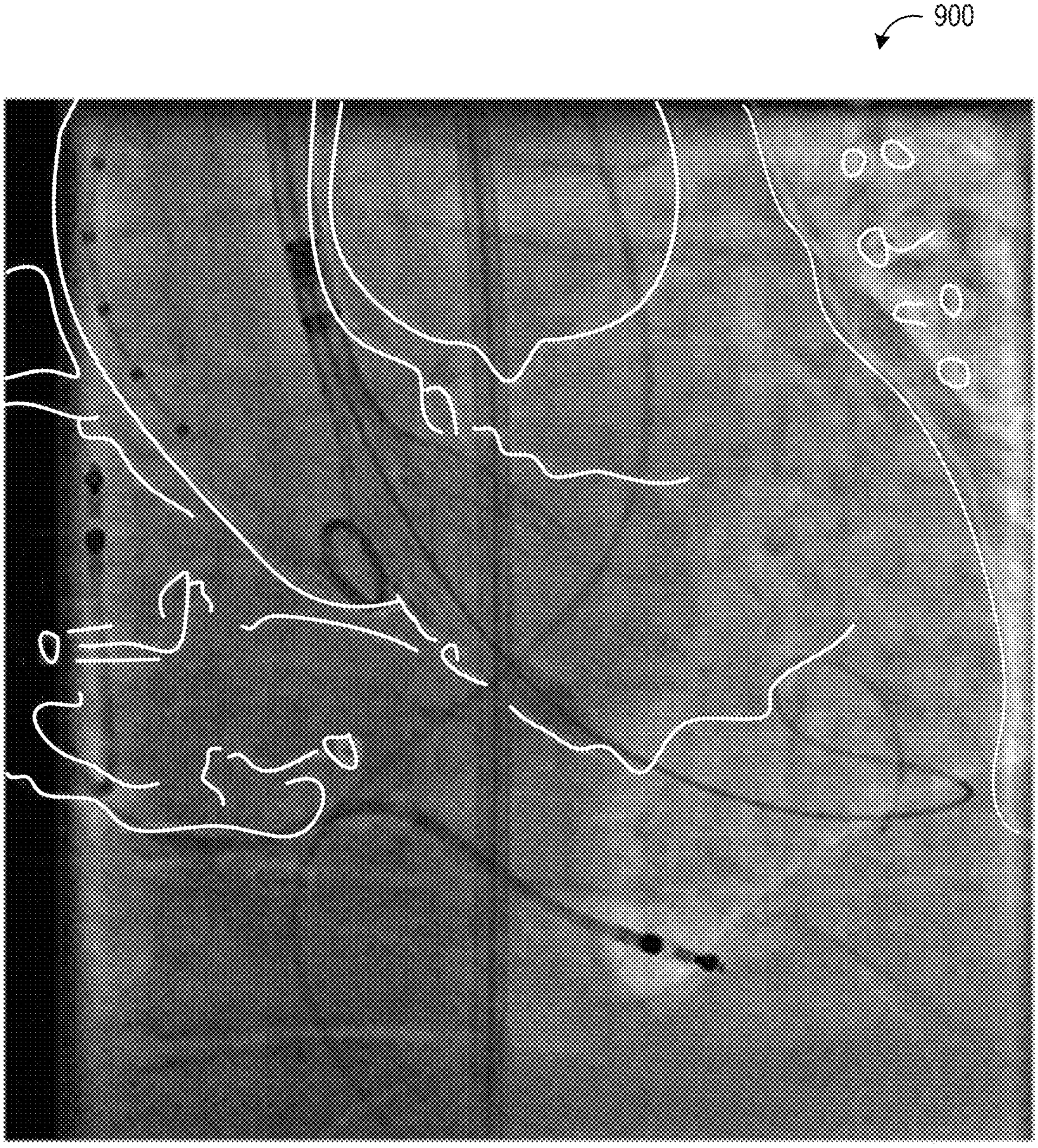
FIG. 9 shows an example fused image with an anatomical silhouette derived from image data and presented in multi planar reformatting (MPR)
Figure 10:
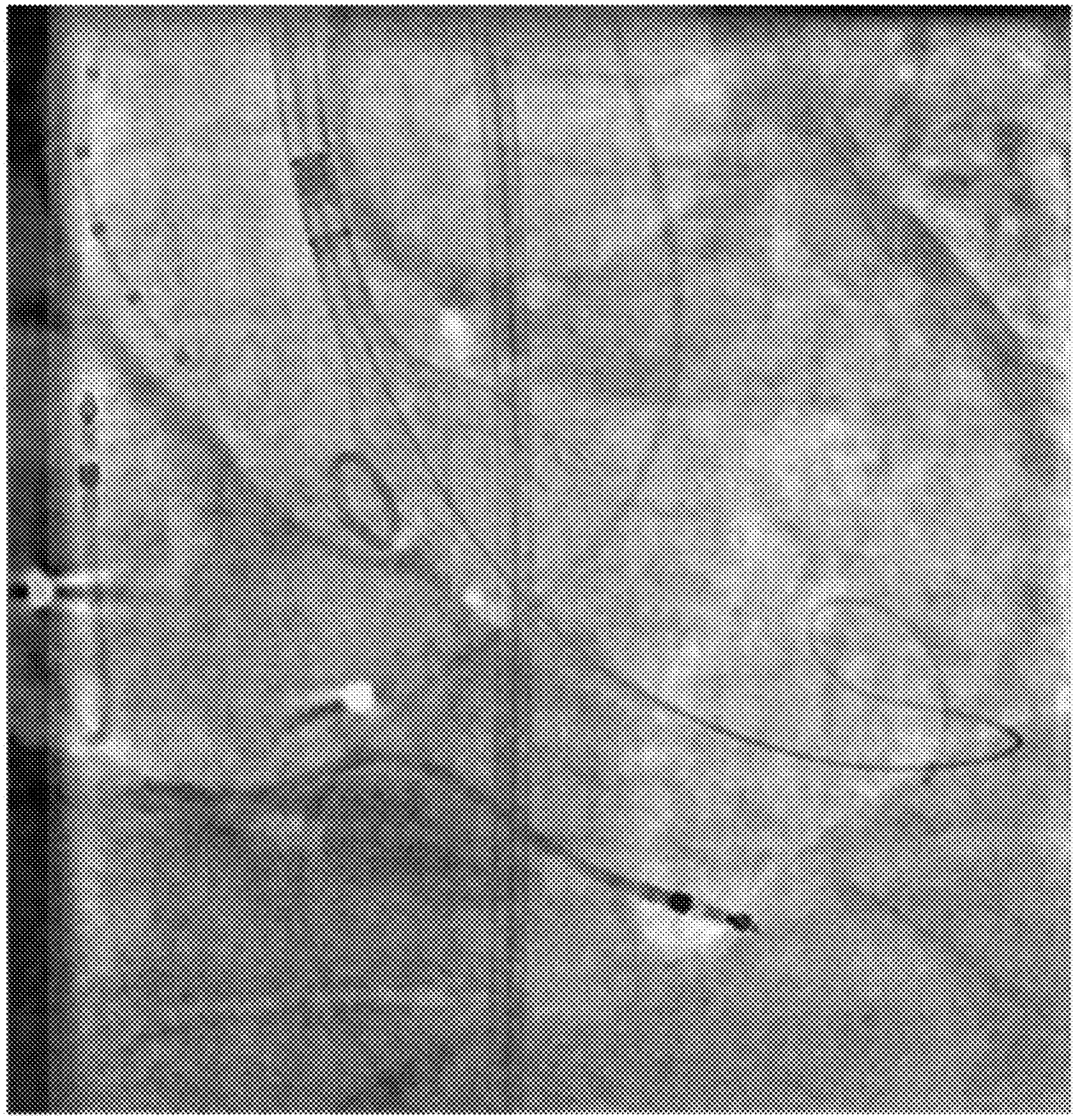
FIG. 10 shows an example fused image with an anatomical silhouette derived from image data and a MPR image.

FIG. 9 shows a second fused image 900. The second fused image 900 may be generated by fusing live X-ray image data and segmented 3D image data, as described with respect to FIGS. 4-7. Specifically, the second fused image 900 includes the anatomical silhouette that is automatically derived from the 3D image data, and presents the 3D image data in an MPR view (e.g., MPR visualization). As described with respect to FIG. 8, this provides visualization of a structure that may itself not be segmented, and is instead shown in the silhouette view. This may reduce processing demand, as well as memory storage demand and network traffic demand to send, receive, and process (e.g., segment) multiple images prior to image registration FIG. 10 shows a third fused image 1000. The third fused image 1000 may be generated by fusing live X-ray image data and segmented 3D image data as described with respect to FIGS. 4-7. Specifically, the third fused image 1000 includes a silhouette of the anatomical ROI automatically derived from the 3D image data that have been processed to generate a MPR view.

Figure 11:
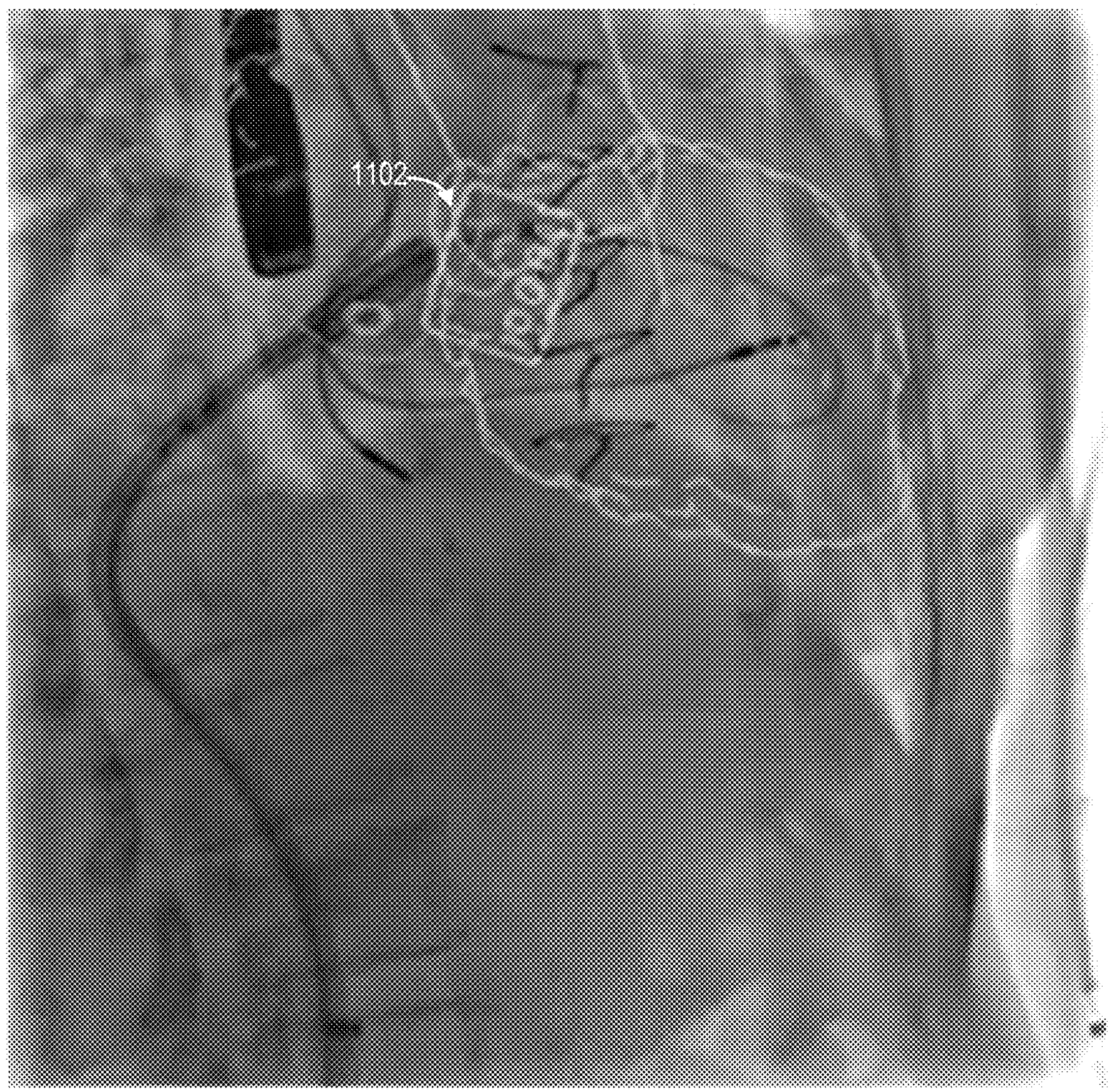
FIG. 11 shows an example fused image with a planning information overlay.

FIG. 11 shows a fourth fused image 1100. The fourth fused image 1100 may be generated by fusing live X-ray image data and segmented 3D image data as described with respect to FIGS. 4-7. Specifically, the fourth fused image 1100 includes a segmented model (e.g., outline of the anatomical ROI from the silhouette view) and therapy plan data. The therapy plan data shows a planned prosthesis 1102 overlaid onto the fused image of the 3D image data and the live X-ray image. The fourth fused image 1100 shows the planned prosthesis with respect to the left ventricle, the left aorta, and the left atrium.

Figure 12:
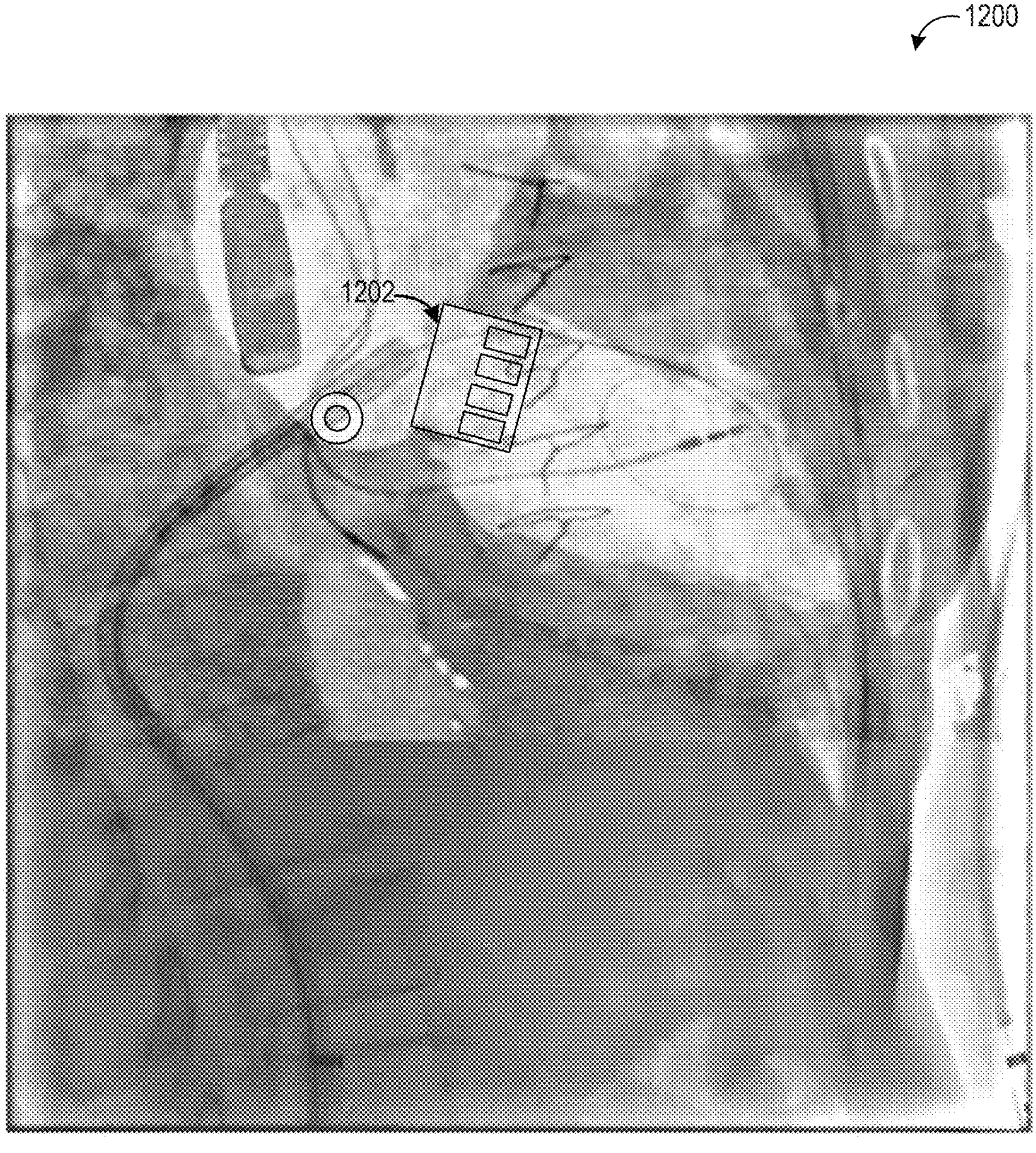
FIG. 12 shows an example fused image comprising a MPR view, a maximum intensity projection (MIP) view, and therapy plan data.
Figure 13:
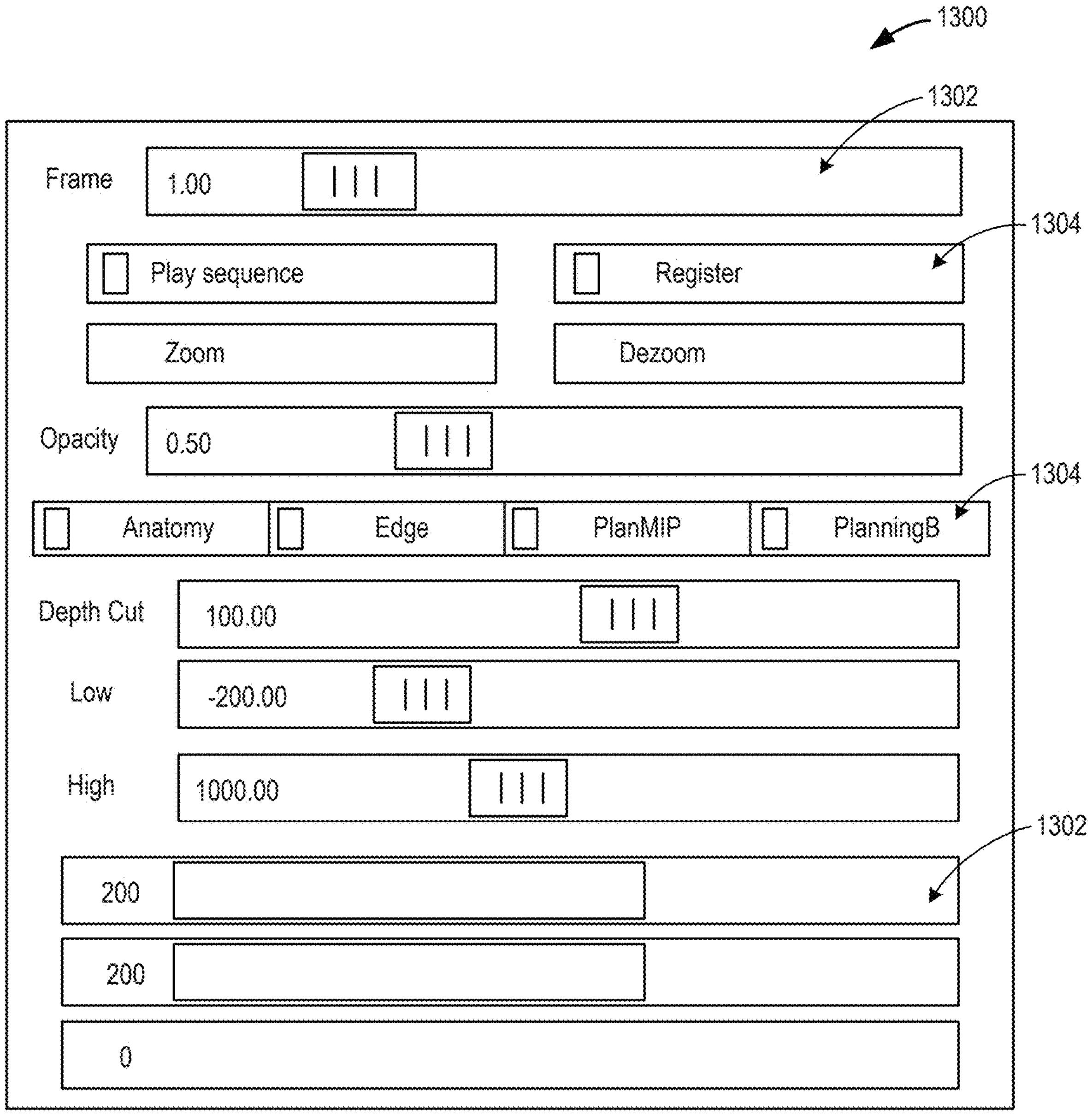
FIG. 13 shows an example user interface used to control image fusion generation.

FIG. 12 shows a fifth fused image 1200. The fifth fused image 1200 may be generated by fusing live X-ray image data and segmented 3D image data as described with respect to FIGS. 4-7. Specifically, the fifth fused image 1200 is generated by fusing live X-ray image data with a MPR view having a MIP applied thereto, and fused therapy plan data. The therapy plan data shows a planned prosthesis 1202 overlaid onto the fused image of the 3D image data and the live X-ray image.

In this way, visualization of different MPR at different depths corresponding to a given configuration of an X-ray imaging chain may be enabled. Processing of the CT or CBCT data with a 3D edge detector is provided, which may assist in increasing an accuracy of silhouette-type rendering of images. Additionally, handling of registration as with standard fusion of segmented models is achieved. A user may benefit from visualization of structures that may not be conventionally segmented, which further assists in automatic image registration by the method. The methods provide a simplified workflow for integration of CT/CBCT images in X-ray images without 3D segmentation of the CT/CBCT images. Additionally, a new strategy for registration is provided, as key anatomical details are displayed, though not segmented and therefore not available for registration. Integration of a 3D edge detector enables automation of preparation of a silhouette view of the anatomy.

The disclosure also provides support for a method, comprising: obtaining three-dimensional (3D) image data of an anatomical region of interest (ROI) of a patient, applying a multi-plane reformation (MPR) tool to the 3D image data to automatically select a slice of the 3D image data that includes the anatomical ROI and corresponds to a view of the anatomical ROI that is shown in a live x-ray image data, fusing the 3D image data with the live x-ray image data without use of a 3D viewer to generate a fused live image comprising 3D image data and live x-ray image data of the anatomical ROI, and outputting the fused live image for display and/or storage. In a first example of the method, the method further comprises: applying a 3D edge detector to the 3D image data, the 3D edge detector configured to automatically identify one or more anatomical structures and generate an outline of the one or more anatomical structures to prepare a silhouette view of the anatomical ROI. In a second example of the method, optionally including the first example, the 3D image data and the live x-ray image data are fused using the silhouette view. In a third example of the method, optionally including one or both of the first and second examples, the slice of the 3D image data that is automatically selected by the MPR tool is derived from a position of an x-ray source and/or an x-ray detector of an x-ray imaging system. In a fourth example of the method, optionally including one or more or each of the first through third examples, the method further comprises: obtaining therapy plan data of the anatomical ROI of the patient, and fusing the therapy plan data to the fused live image. In a fifth example of the method, optionally including one or more or each of the first through fourth examples, therapy plan data comprises a simulated prosthesis position, size, and/or location in the anatomical ROI. In a sixth example of the method, optionally including one or more or each of the first through fifth examples, the therapy plan data comprises a simulated incision in the anatomical ROI. In a seventh example of the method, optionally including one or more or each of the first through sixth examples, obtaining 3D image data of the anatomical ROI of the patient further comprises applying a maximum intensity operator to the 3D image data to identify a view of the anatomical ROI having a maximum intensity of the 3D image data. In an eighth example of the method, optionally including one or more or each of the first through seventh examples, the method further comprises: applying 3D segmentation to the 3D image data to identify the anatomical ROI in the 3D image data.

The disclosure also provides support for a method, comprising: obtaining a first image data of an anatomical region of interest (ROI) of a patient, the first image data acquired with a first imaging modality, detecting three-dimensional (3D) edges of one or more anatomical structures of the first image data by automatically identifying one or more anatomical structures in the first image data and generating an outline of the one or more anatomical structures to generate a 3D model of the first image data with a silhouette rendering of the anatomical ROI, obtaining a second image data of the anatomical ROI of the patient, the second image data acquired with a second imaging modality, registering the 3D model of the first image data with the second image data, generating a fused image of the 3D model of the first image data and the second image data, and outputting the fused image of the anatomical ROI for display and/or storage. In a first example of the method, registering the 3D model of the first image data with the second image data comprises automatically selecting a multi-plane reformatted view of the 3D model based on the second image data. In a second example of the method, optionally including the first example, registering the 3D model of the first image data with the second image data comprises automatically selecting a simple visualization of the 3D model using a maximum intensity operator. In a third example of the method, optionally including one or both of the first and second examples, the first image data comprises 3D computed tomography (CT) image data. In a fourth example of the method, optionally including one or more or each of the first through third examples, the second image data comprises live X-ray image data. In a fifth example of the method, optionally including one or more or each of the first through fourth examples, the first image data comprises 3D CT and/or CBCT image data captured during capture of the second image data. In a sixth example of the method, optionally including one or more or each of the first through fifth examples, the method further comprises: applying a planning information overlay to the fused image to simulate a position, orientation, and/or size of a therapy plan for the anatomical ROI. In a seventh example of the method, optionally including one or more or each of the first through sixth examples, the method further comprises: applying 3D segmentation to the first image data to identify the anatomical ROI in the first image data.

The disclosure also provides support for a system, comprising: a processor, and non-transitory memory storing instructions executable by the processor to: obtaining a first image data of an anatomical region of interest (ROI) of a patient, the first image data acquired with a first imaging modality, using a trained deep learning model to automatically identify a morphology of one or more anatomies present in the first image data by comparing the first image data to defined anatomy morphologies, and generating an outline of the morphology of each of the one or more anatomies to generate a 3D model of the first image data with a silhouette rendering of the anatomical ROI, obtaining a second image data of the anatomical ROI of the patient, the second image data acquired with a second imaging modality, registering the 3D model of the first image data with the second image data, generating a fused image of the 3D model of the first image data and the second image data, and outputting the fused image of the anatomical ROI for display and/or storage. In a first example of the system, the system further comprises: an X-ray source and an X-ray detector configured to capture a live X-ray image of the anatomical ROI positioned in a field of view (FOV) of the X-ray detector. In a second example of the system, optionally including the first example, the processor is further configured to adjust a position of the X-ray source and/or the X-ray detector to adjust the FOV of the X-ray detector.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional such elements not having that property. The terms “including” and “in which” are used as the plain-language equivalents of the respective terms “comprising” and “wherein.” Moreover, the terms “first,” “second,” and “third,” etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

obtaining three-dimensional (3D) image data of an anatomical region of interest (ROI) of a patient;

applying a multi-plane reformation (MPR) tool to the 3D image data to automatically select a slice of the 3D image data that includes the anatomical ROI and corresponds to a view of the anatomical ROI that is shown in a live x-ray image data;

via a trained deep learning model, automatically identifying a morphology of one or more anatomies present in the anatomical ROI by comparing the slice of the 3D image data to defined anatomy morphologies, and generating an outline of the morphology of each of the one or more anatomies to generate a 3D model of the 3D image data with a silhouette rendering of the anatomical ROI;

via an image processing system, fusing the 3D image data with the live x-ray image data using the silhouette rendering and without use of a 3D viewer to generate a fused live image comprising 3D image data and live x-ray image data of the anatomical ROI; and outputting the fused live image for display and/or storage.

2. The method of claim 1, wherein the slice of the 3D image data that is automatically selected by the MPR tool is derived from a position of an x-ray source and/or an x-ray detector of an x-ray imaging system.

3. The method of claim 1, further comprising:

obtaining therapy plan data of the anatomical ROI of the patient; and fusing the therapy plan data to the fused live image.

4. The method of claim 3, wherein therapy plan data comprises a simulated prosthesis position, size, and/or location in the anatomical ROI.

5. The method of claim 3, wherein the therapy plan data comprises a simulated incision in the anatomical ROI.

6. The method of claim 1, wherein obtaining 3D image data of the anatomical ROI of the patient further comprises applying a maximum intensity operator to the 3D image data to identify a view of the anatomical ROI having a maximum intensity of the 3D image data.

7. The method of claim 1, further comprising applying 3D segmentation to the 3D image data to identify the anatomical ROI in the 3D image data.

8. A method, comprising:

obtaining a first image data of an anatomical region of interest (ROI) of a patient, the first image data acquired with a first imaging modality;

detecting three-dimensional (3D) edges of one or more anatomical structures of the first image data via a trained deep learning model configured to automatically identify one or more anatomical structures in the first image data by comparing the first image data to defined anatomy morphologies and generating an outline of the one or more anatomical structures to generate a 3D model of the first image data with a silhouette rendering of the anatomical ROI;

obtaining a second image data of the anatomical ROI of the patient, the second image data acquired with a second imaging modality;

registering the 3D model of the first image data with the second image data by spatially aligning the anatomical ROI of the first image data with the anatomical ROI of the second image data;

generating a fused image of the 3D model of the first image data and the second image data by performing pixel-by-pixel combination of the first image data and the second image data; and outputting the fused image of the anatomical ROI for display and/or storage.

9. The method of claim 8, wherein registering the 3D model of the first image data with the second image data comprises automatically selecting a multi-plane reformatted view of the 3D model based on the second image data.

10. The method of claim 8, wherein registering the 3D model of the first image data with the second image data comprises automatically selecting a simple visualization of the 3D model using a maximum intensity operator.

11. The method of claim 8, wherein the first image data comprises 3D computed tomography (CT) image data.

12. The method of claim 8, wherein the second image data comprises live X-ray image data.

13. The method of claim 8, wherein the first image data comprises 3D CT and/or CBCT image data captured during capture of the second image data.

14. The method of claim 8, further comprising applying a planning information overlay to the fused image to simulate a position, orientation, and/or size of a therapy plan for the anatomical ROI.

15. The method of claim 8, further comprising applying 3D segmentation to the first image data to identify the anatomical ROI in the first image data.

16. A system, comprising:

a processor; and non-transitory memory storing instructions executable by the processor to:

obtain a first image data of an anatomical region of interest (ROI) of a patient, the first image data acquired with a first imaging modality;

use a trained deep learning model to automatically identify a morphology of one or more anatomies present in the first image data by comparing the first image data to defined anatomy morphologies, and generating an outline of the morphology of each of the one or more anatomies to generate a 3D model of the first image data with a silhouette rendering of the anatomical ROI;

obtain a second image data of the anatomical ROI of the patient, the second image data acquired with a second imaging modality;

register the 3D model of the first image data with the second image data;

generate a fused image of the 3D model of the first image data and the second image data; and output the fused image of the anatomical ROI for display and/or storage.

17. The system of claim 16, further comprising an X-ray source and an X-ray detector configured to capture a live X-ray image of the anatomical ROI positioned in a field of view (FOV) of the X-ray detector.

18. The system of claim 17, wherein the processor is further configured to adjust a position of the X-ray source and/or the X-ray detector to adjust the FOV of the X-ray detector.

* * * * *